United States Patent [19]

Klauke et al.

[11] 3,984,468

[45] Oct. 5, 1976

[54] HERBICIDAL N-TRIFLUOROMETHYLMERCAPTOPHENYL UREAS

[75] Inventors: Erich Klauke, Odenthal-Hahnenberg; Engelbert Kühle, Berg. Gladbach; Ludwig Eue, Cologne-Stammhelm; Helmuth Hack, Cologne-Buchheim, all of Germany

[73] Assignee: Bayer Aktiengesellschaft, Leverkusen, Germany

[22] Filed: Aug. 8, 1974

[21] Appl. No.: 495,760

Related U.S. Application Data

[63] Continuation of Ser. No. 211,781, Dec. 23, 1971, abandoned, which is a continuation of Ser. No. 749,285, Aug. 1, 1968, abandoned.

[30] Foreign Application Priority Data

Aug. 12, 1967 Germany.................................. 53225

[52] U.S. Cl................................ 260/553 A; 71/98; 71/120
[51] Int. Cl.². ....................................... C07C 127/19
[58] Field of Search................................ 260/553 A

[56] References Cited

UNITED STATES PATENTS

| | | | |
|---|---|---|---|
| 2,050,582 | 8/1936 | Orthner et al. | 260/553 A X |
| 3,326,663 | 6/1967 | Soloway et al. | 260/553 A X |
| 3,931,312 | 1/1976 | Klauke et al. | 260/553 A |

FOREIGN PATENTS OR APPLICATIONS

| | | | |
|---|---|---|---|
| 1,532,014 | 7/1968 | France | |
| 1,576,194 | 7/1969 | France | |
| 1,912,544 | 10/1969 | Germany | 260/553 A |
| 1,291,733 | 4/1969 | Germany | 260/553 A |

*Primary Examiner*—Daniel E. Wyman
*Assistant Examiner*—Thomas A. Waltz
*Attorney, Agent, or Firm*—Burgess, Dinklage & Sprung

[57] ABSTRACT

N-(trifluoromethylmercapto-phenyl)-N'-alkyl and -N',N'-dialkyl ureas which possess herbicidal properties, and which may be produced by conventional methods.

6 Claims, No Drawings

HERBICIDAL N-TRIFLUOROMETHYLMERCAPTOPHENYL UREAS

This is a continuation of application Ser. No. 211,781, filed Dec. 23, 1971, which itself is a continuation of Ser. No. 749,285, filed Aug. 1, 1968, both now abandoned.

The present invention relates to and has for its objects the provision for particular new N-aryl ureas which possess valuable, especially selective, herbicidal properties, active compositions in the form of mixtures of such compounds with solid and liquid dispersible carrier vehicles, and methods for producing such compounds and for using such compounds in a new way, especially for combating weeds, undesired plants, and the like, with other and further objects becoming apparent from a study of the within specification and accompanying examples.

It is know tht N-aryl-N'-alkyl ureas can be used as herbicides. It is further known that N-(3-trifluoromethylphenyl)-N',N'-dimethyl urea (A) can be used as a selective herbicide (cf. U.S. Pat. No. 3,134,665), and such compound has attained a considerable importance in practice.

It has now been found, in accordance with the present invention, that the particular new N-aryl ureas, i.e. N-(3- and 4-trifluoromethylmercapto-phenyl)-N'-alkyl and -N',N'-dialkyl ureas having the general formula

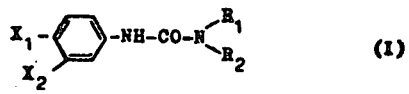
(I)

in which $X_1$ and $X_2$ are trifluoromethylmercapto, chlorine or hydrogen, $X_1$ or $X_2$ being trifluoromethylmercapto, $R_1$ is selected from the group consisting of hydrogen and alkyl having 1–4 carbon atoms, and $R_2$ is alkyl having 1–4 carbon atoms, exhibit strong herbicidal, in particular selective herbicidal, properties.

It has been furthermore found, in accordance with the present invention, that a versatile and smooth process for the production of the particular new N-aryl areas of formula (I) above in favorable yields may be provided, which comprises reacting an isocyanate having the formula

(IIa)

in which $X_1$ and $X_2$ are the same as defined above, with an amine having the formula

(IIb)

in which $R_1$ and $R_2$ are the same as defined above, in the presence of a diluent.

It is very surprising that the particular new active compounds of the present invention exhibit a higher herbicidal activity, combined with selectivity in respect of agricultural cultivated plants, than the previously known trifluoromethylphenyl urea.

When 4-trifluoromethylmercapto-phenyl isocyanate and dimethyl amine are used, the reaction of the production process of the present invention can be represented by the following equation:

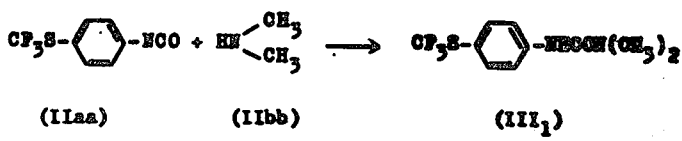

(IIaa)　　　(IIbb)　　　(III₁)

As further examples of isocyanates, there are mentioned: 3-chloro-4-trifluoromethylmercapto-phenyl isocyanate, 3-trifluoromethylmercapto-phenyl isocyanate and 3-trifluoromethylmercapto-4-chlorophenyl isocyanate.

Examples of suitable amines include methyl amine, dimethyl amine, methyl-ethyl amine, propyl amine, butyl amine, methyl-butyl amine and di-isopropyl amine.

As diluent, there may be used for example water or an inert organic solvent. Preferred organic solvents include ethers, such as dioxan, hydrocarbons, such as benzene, and chlorinated hydrocarbons, such as benzene, and chlorinated hydrocarbons, such as chlorobenzene.

The reaction temperatures can be varied within a fairly wide range; in general, the reaction is carried out at substantially between about 10°–80°C, preferably at about 20°–50°C.

Approximately equimolar amounts of the isocyanate and amine may be used, but an excess of amine is not detrimental. Working up may take place in the usual manner.

Advantageously, the particular new active compounds of the present invention exhibit strong herbicidal properties. The instant compounds can be used for the destruction of weeds. As weeds in the widest sense are deemed plants which grow in cultivations or in other places where they are not desired. Whether the particular new active compounds of the present invention act as total or as selective substances depends essentially on the amount applied, as the artisan will appreciate.

The instant active compounds can be used for example in the case of the following plants: dicotyledons, such as mustard (Sinapis), cress (Lepidium), cleaver (Galium), common chick-weed (Stellaria), mayweed (matricaria), smallflower Galinsoga (Galinsoga), fa-then (Chenopodium), stinging nettle (Urtica), groundsel (Senecio), cotton (Gossypium), beets (Beta), carrots (Daucus), beans (Phaseolus), potatoes (Solanum), coffee (Coffea); monocotyledons, such as timothy (Phleum), bluegrass (Poa), fescue (Festuca), goosegrass (Eleusine), foxtail (Setaria), ryegrass (Lolium), cheat (Bromus), barnyard grass (Echinochloa), maize (Zea), rice (Oryza), oats (Avena), barley (Hordeum), wheat (Triticum), millet (Panicum), sugar cane (Saccharum); and the like.

The particular new active compounds of the present invention are especially well suited for selective weed control in oats, wheat, maize and cotton cultivation.

The particular new active compounds of the present invenion ar especially well suited for selective weed control in oats, wheat, maize and cotton cultivation.

The particular active compounds to be used according to the instant invention can be utilized, if desired, in the form of the usual formulations or compositions with diluents or extenders, i.e. dispersible carrier vehicles, such as solutions, emulsions, suspensions, emulsifiable concentrates, spray powders, pastes, soluble powders, dusting agents, granules, etc. These are prepared in known manner, for instance by extending the active compounds with dispersible liquid diluent carriers and/or dispersible solid carriers optionally with the use of carrier vehicle assistants, e.g. surface-active agents, including emulsifying agents and/or dispersing agents, whereby, for example, in the case where water is used as diluent, organic solvents may be added as auxiliary solvents (cf. Agricultural Chemicals, March 1960, pp. 35–38). The following may be chiefly considered for use as carrier vehicles for this purpose: dispersible liquid diluent carriers including inert organic solvents, such as aromatic hydrocarbons (for instance, benzene, toluene, xylene, etc.), halogenated, especially chlorinated, aromatic hydrocarbons (for instance, chlorobenzenes), paraffins (for instance, petroleum fractions), chlorinated aliphatic hydrocarbons (for instance, methylene chloride, etc.), alcohols (for instance, methanol, ethanol, propanol, butanol, etc.), ethers, ether-alcohols (for instance, glycol monomethyl ether, etc.), amines (for instance, ethanolamine, etc.), amides (for instance, dimethyl formamide, etc.), sulfoxides (for instance, dimethyl sulfoxide, etc.) ketones (for instance, acetone, etc.), and/or water; as well as dispersible finely divided solid carriers, such as ground natural minerals (for instance, kaolins, alumina, silica, chalk, i.e. calcium carbonate, talc, kieselguhr, etc.), and ground synthetic minerals (for instance, highly dispersed silicic acid, silicates, e.g. alkali silicates, etc.); whereas the following may be chiefly considered for use as carrier vehicle assistance, e.g. surface-active agents, for this purpose: emulsifying agents, such as nonionic and/or anionic emulsifying agents (for instance, polyethylene oxide esters of fatty acids, polyethylene oxide ethers of fatty alcohols, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

As wil be appreciated by the artisan, the active compounds according to the instant invention may be employed alone or in the form of mixtures with one another and/or with such solid and/or liquid dispersible carrier vehicles and/or with other known compatible active agents, especially plant protection agents, such as other herbicides, fungicides, insecticides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.005–10%, preferably 0.01–1%, by weight of the mixture. Thus, the present invention contemplates over-all compositions which comprise mixtures of a dispersible carrier vehicle such as (1) a dispersible inert finely divided carrier solid, and/or (2) a dispersible carrier liquid such as an inert organic solvent and/or water preferably including a surface-active amount of a carrier vehicle assistant, e.g. a surface-active agent, such as an emulsifying agent and/or a dispersing agent, and an amount of the active compound which is effective for the purpose in question and which is generally between about 0.005–95%, and preferably 0.01–95%, by weight of the mixture.

In particular, the amount of active compound per unit area varies according to the purpose intended and the mode of application. In general, substantially between about 0.5–10 kg of active compound per hectare are applied, preferably between about 1–8 kg per hectare.

The active compounds can also be used in accordance with the well known ultra-low-volume process with good success, i.e. by applying such compound if normally a liquid, or by applying a liquid composition containing the same, via very effective atomizing equipment in extremely finely divided form, i.e. mist form, for example by airplane crop spraying techniques. Only a few liters/hectare are needed, and often amounts up to about 1 quart/acre, preferably 2–16 fluid ounces/acre, are sufficient. In this process it is possible to use highly concentrated liquid compositions with said liquid carrier vehicles containing from about 40 to about 95% by weight of active compound or even the 100% active substance alone, e.g. about 40–100% by weight of the active compound.

While the active compounds can be used according to the pre-emergence method, they are particularly effective when used according to the post-emergence method.

Furthermore, the present invention contemplates methods of selectively controlling or combating undesired plants, e.g. weeds and the like, which comprise applying to at least one of (a) such weeds ad (b) their habitat, i.e. the locus to be protected, a herbicidally effective amount of the particular active compound of the invention alone or together with a carrier vehicle as noted above. The instant formulations or compositions are applied in the usual manner, for example by spraying, atomizing, scattering, dusting, watering, sprinkling, and the like, whether for pre-emergence application to the soil or post-emergence application to the weeds.

It will be realized, of course, that in connection with the pre-emergence use of the instant compounds as well as the post-emergence use thereof, the concentration of the particular active compund utilized in admixture with the carrier vehicle will depend upon the intended application and may be varied within a fairly wide range depending upon the weather conditions, the purpose for which the active compound is used, e.g. as total or only selective herbicidal effect, and the plants which are to be controlled or protected. Therefore, in special cases, it is possible to go above or below the aforementioned concentration ranges.

The following Examples illustrate, without limitation, the herbicidal activity of the particular active compounds of the present invention.

EXAMPLE 1

Pre-emergence test

The particular active compounds tested, the amounts applied and the results obtained can be seen from Table 1.

Table I

| Active Compound | Pre-emergence test Amount applied of active compound kg/hectare | Echino-chloa | Cheno-podium | Sinapis | Cotton | Wheat |
|---|---|---|---|---|---|---|
| (A) 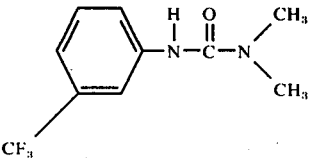 (known) | 5<br>2.5 | 5<br>5 | 5<br>5 | 5<br>5 | 0<br>0 | 4<br>4 |
| (III$_2$) 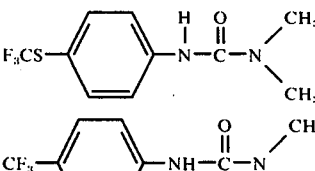 | 5<br>2.5 | 5<br>5 | 5<br>5 | 5<br>5 | 0<br>0 | 1<br>0 |
| 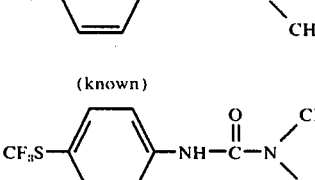 (known) | 5<br>2.5 | 5<br>4 | 5<br>4 | 5<br>5 | 2-3<br>1 | 5<br>4 |
| 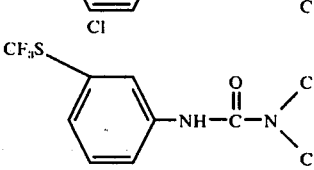 | 5<br>2.5 | 4<br>3 | 5<br>3 | 5<br>3 | 0<br>0 | 0<br>0 |
|  | 5<br>2.5 | 5<br>5 | 5<br>5 | 5<br>4 | 0<br>0 | 1<br>0 |

| | |
|---|---|
| Solvent: | 5 parts by weight acetone |
| Emulsifier: | 1 part by weight alkylaryl polyglycol ether |

To produce a suitable preparation of the particular active compound, 1 part by weight of such active compound is mixed with the stated amount of solvent, the stated amount of emulsifier is then added and the resulting concentrate is diluted with water to the desired final concentration.

Seeds of the test plants are sown in normal soil and, after 24 hours, watered with the active compound preparation. It is expedient to keep constant the amount of water per unit area. The concentration of the given active compound in the preparation is of no importance, only the amount of active compound applied per unit area being decisive. After three weeks, the degree of damage to the test plants is determined and characterized by the values 0–5, which have the following meaning:

0 no effect
1 slight damage or delay in growth
2 marked damage or inhibition of growth
3 heavy damage and only deficient development or only 50% emerged
4 plants partially destroyed after germination or only 25% emerged
5 plants completely dead or not emerged.

EXAMPLE 2

Post-emergence test

| | |
|---|---|
| Solvent: | 5 parts by weight acetone |
| Emulsifier: | 1 part by weight alkylaryl polyglycol ether |

To produce a suitable preparation of the particular active compound, 1 part by weight of such active compound is mixed with the stated amount of solvent, the stated amount of emulsifier is then added and the resulting concentrate is diluted with water to the desired final concentration.

Test plants which have a height of about 5–15 cm. are sprayed with the active compound preparation until just dew moist. After three weeks, the degree of damage to the plants is determined and characterized by the values 0–5, which have the following meaning:

0 no effect
1 a few slightly burnt spots
2 marked damage to leaves
3 some leaves and parts of stalks partially dead
4 plant partially destroyed
5 plant completely dead.

The particular active compounds tested, their concentrations and the results obtained can be seen from Table 2.

Table 2

Post-emergence test

| Active compound | Concentration of active compound % | Echino-chloa | Cheno-podium | Sina-pis | Galin-soga | Stella-ria | Urtica | Metri-caria | Wheat |
|---|---|---|---|---|---|---|---|---|---|
| (A) 3-CF₃-C₆H₄-N(H)-C(O)-N(CH₃)₂ (known) | 0.025 | 4 | 5 | 5 | 5 | 5 | 4–5 | 3 | 0 |
|  | 0.01 | 1 | 5 | 4 | 5 | 5 | 3 | 2 | 0 |
|  | 0.005 | 1 | 3–4 | 3 | 3 | 3–4 | 2 | 1 | 0 |
| (III₁) 4-F₃CS-C₆H₄-N(H)-C(O)-N(CH₃)₂ | 0.025 | 5 | 5 | 5 | 5 | 5 | 5 | 5 | 0 |
|  | 0.01 | 3–4 | 5 | 5 | 5 | 5 | 5 | 3–4 | 0 |
|  | 0.005 | 2 | 5 | 4–5 | 5 | 5 | 3 | 2 | 0 |
| 4-CF₃-C₆H₄-NH-C(O)-N(CH₃)₂ (known) | 0.025 | 4 | 5 | 5 | 5 | 5 | 5 | 3–4 | 3 |
|  | 0.01 | 2 | 4–5 | 4 | 5 | 4 | 4 | 3 | 2 |
|  | 0.005 | 1 | 4 | 3 | 3 | 3–4 | 3 | 1 | 0 |
| 3-Cl, 4-CF₃S-C₆H₃-NH-C(O)-N(CH₃)₂ | 0.025 | 5 | 5 | 5 | 5 | 5 | 5 | 5 | 4 |
|  | 0.01 | 4–5 | 5 | 5 | 5 | 5 | 5 | 4–5 | 3–4 |
|  | 0.005 | 4 | 5 | 5 | 5 | 5 | 4–5 | 3 | 3 |
| 3-CF₃S-C₆H₄-NH-C(O)-N(CH₃)₂ | 0.025 | 5 | 5 | 5 | 4 | 5 | 5 | 4 | 0 |
|  | 0.01 | 3–4 | 5 | 4 | 3 | 4–5 | 4 | 3 | 0 |
|  | 0.005 | 2 | 4 | 3 | 2 | 3–4 | 2–3 | 2 | 0 |

The process for producing the particular new compounds of the present invention is illustrated, without limitation, by the following further Examples.

EXAMPLE 3

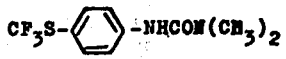 (III₄)

12g 4-trifluoromethylmercapto-phenyl isocyanate are added dropwise at room temperature to 50 ml of a 20% aqueous solution of dimethyl amine. The temperature is allowed to rise to about 35°C, stirring is effected until the reaction subsides, and the crystalline product is filtered off with suction. 10g of the above urea, i.e. N-(4-trifluoromethylmercapto-phenyl)-N',N'-dimethyl urea, of m.p. 148°–149°C are obtained.

The 4-trifluoromethylmercapto-phenyl isocyanate starting material is obtained in particularly favorable manner from 4-trichloromethylmercapto-phenyl isocyanate ($n_D^{20}$: 1.6125) by reaction with anhydrous hydrofluoric acid under pressure at temperatures of up to 110°C as water-white liquid of boiling point 91°–92°C/17mm Hg and refractive index $n_D^{20}$: 1.5104.

In analogous manner are prepared:

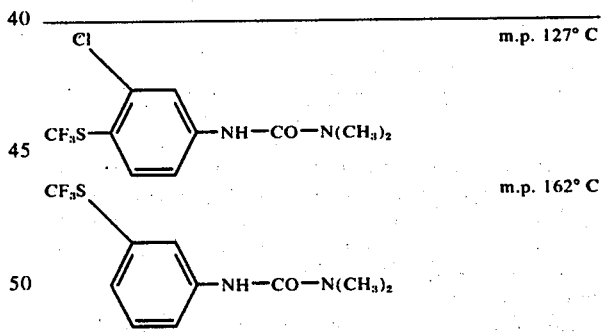

EXAMPLE 4

Using corresponding molar amounts of 4-trifluoromethylmercapto-phenyl isocyanate with each of the following amines, respectively, in accordance with the procedure of Example 3, as the case may be:
a. methyl amine, and
b. di-tert.-butyl amine,
the corresponding final compounds, respectively, are produced:
a'. N-(4-trifluoroemthylmercapto-phenyl)-N'-methyl urea; and
b'. N-(4-trifluoromethylmercapto-phenyl)-N',N'-di-tert.-butyl urea.

Advantageously, in accordance with the present invention, in the foregoing formulae:

$X_1$ represents trifluoromethylmercapto or hydrogen;

$X_2$ represents hydrogen, trifluoromethylmercapto or chlorine;

$R_1$ represents hydrogen or alkyl having 1–4 carbon atoms such as methyl, ethyl, n-propyl, isopropyl, n-butyl, isobutyl, sec.-butyl, tert.-butyl, and the like, especially methyl; and $R_2$ represents alkyl having 1–4 carbon atoms such as methyl to tert.-butyl inclusive, and the like, as defined above, especially methyl;

$R_1$ and $R_2$ being the same or different.

In accordance with a particular feature of the present invention, N-(3- and 4-trifluoromethylmercapto-phenyl)-N'-alkyl and -N',N'-dialkyl ureas are contemplated which have the formula

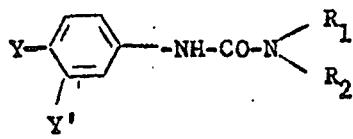

in which $R_1$ is hydrogen or $C_{1-4}$ alkyl and $R_2$ is $C_{1-4}$ alkyl, $R_1$ and $R_2$ preferably being the same when $R_1$ is also $C_{1-4}$ alkyl.

It will be realized by the artisan that all of the foregoing compounds contemplated by the present invention possess the desired selective or total herbicidal properties, and especially the capability of selectively destroying weeds, as well as a comparatively low toxicity toward warm-blooded creatures and a concomitantly low phytotoxicity with respect to higher plants, enabling such compounds to be used with correspondingly favorable compatibility with warm-blooded creatures and higher plants for more effective control and/or elimination of weeds by selective application of such compounds to such weeds and/or their habitat. Nevertheless, the instant compounds possess total herbicidal action when used in large quantities, although selective herbicidal action is otained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention which is to be limited only by the scope of the appended claims.

What is claimed is:

1. N-trifluoromethylmercapto-phenyl urea having the formula

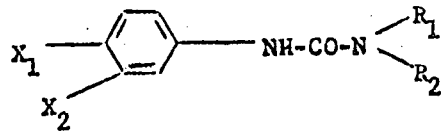

in which $X_1$ is selected from the group consisting of trifluoromethylmercapto and hydrogen, $X_2$ is selected from the group consisting of trifluoromethylmercapto, chloro and hydrogen, one of $X_1$ and $X_2$ being trifluoromethylmercapto, $R_1$ is selected from the group consisting of hydrogen and alkyl having 1 to 4 carbon atoms, and $R_2$ is alkyl having 1 to 4 carbon atoms.

2. Urea according to claim 1 wherein $R_1$ and $R_2$ each respectively is $C_{1-4}$ alkyl.

3. Urea according to claim 1 wherein $R_1$ and $R_2$ are the same $C_{1-4}$ alkyl.

4. Urea according to claim 1 wherein such compound is N-(4-trifluoromethylmercapto-phenyl)-N',N'-dimethyl urea having the formula

5. Urea according to claim 1 wherein such compound is N-(3-trifluoromethylmercapto-phenyl)-N',N'-dimethyl urea having the formula

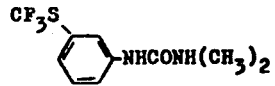

6. Urea according to claim 1 wherein such compound is N-(3-chloro-4-trifluoromethylmercapto-phenyl)-N',N'-dimethyl urea having the formula

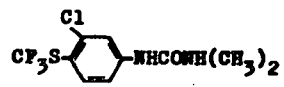

* * * * *